US012776322B2

(12) United States Patent
Okabe et al.

(10) Patent No.: US 12,776,322 B2
(45) **Date of Patent: *Oct. 27, 2026**

(54) BIOMETRIC AUTHENTICATION DEVICE, BIOMETRIC AUTHENTICATION METHOD, AND RECORDING MEDIUM

(71) Applicant: NEC Corporation, Tokyo (JP)

(72) Inventors: Koji Okabe, Tokyo (JP); Takayuki Arakawa, Tokyo (JP); Takafumi Koshinaka, Tokyo (JP)

(73) Assignee: NEC CORPORATION, Tokyo (JP)

(*) Notice: Subject to any disclaimer, the term of this patent is extended or adjusted under 35 U.S.C. 154(b) by 160 days.

This patent is subject to a terminal disclaimer.

(21) Appl. No.: 18/483,905

(22) Filed: Oct. 10, 2023

(65) Prior Publication Data

US 2024/0038243 A1 Feb. 1, 2024

Related U.S. Application Data

(63) Continuation of application No. 17/270,303, filed as application No. PCT/JP2019/032729 on Aug. 22, 2019, now abandoned.

(30) Foreign Application Priority Data

Aug. 31, 2018 (JP) ................................ 2018-162229

(51) Int. Cl.

| | |
|---|---|
| ***G10L 17/06*** | (2013.01) |
| ***A61B 5/117*** | (2016.01) |
| *G06F 21/32* | (2013.01) |

(52) U.S. Cl.

CPC .............. *G10L 17/06* (2013.01); *A61B 5/117* (2013.01); *G06F 21/32* (2013.01)

(58) Field of Classification Search

CPC .......... G10L 17/06; A61B 5/117; G06F 21/32

See application file for complete search history.

(56) References Cited

U.S. PATENT DOCUMENTS

| | | | | |
|---|---|---|---|---|
| 7,088,220 B2 | 8/2006 | Kotzin | | |
| 7,529,379 B2 * | 5/2009 | Zurek | .................... | G06V 40/10 381/328 |

(Continued)

FOREIGN PATENT DOCUMENTS

| | | |
|---|---|---|
| JP | 2000-148985 A | 5/2000 |
| JP | 2002-221990 A | 8/2002 |

(Continued)

OTHER PUBLICATIONS

Mohammed, Safiia, and Michael Hegarty, "Evaluation of Voice & Ear Biometrics Authentication System", Jul. 2017, International Journal of Education and Management Engineering, vol. 7, No. 4, pp. 29-40. (Year: 2017).*

(Continued)

*Primary Examiner* — James Boggs

(74) *Attorney, Agent, or Firm* — Sughrue Mion, PLLC

(57) ABSTRACT

A biometric authentication device is provided with: a replay unit for reproducing a sound; an ear authentication unit for acquiring a reverberation sound of the sound in an ear of a user to be authenticated, extracting an ear acoustic feature from the reverberation sound, and calculating an ear authentication score by comparing the extracted ear acoustic feature with an ear acoustic feature stored in advance; a voice authentication unit for extracting a talker feature from a voice of the user that has been input, and calculating a voice authentication score by comparing the extracted talker feature with a talker feature stored in advance; and an authentication integration unit for outputting an authentication integration result calculated based on the ear authentication score and the voice authentication score. After the sound is output into the ear, a recording unit inputs the voice of the user.

12 Claims, 7 Drawing Sheets

(56) References Cited

U.S. PATENT DOCUMENTS

| | | | | |
|---|---|---|---|---|
| 8,548,208 | B2 * | 10/2013 | Schultz | G06F 21/32 340/5.82 |
| 9,100,825 | B2 | 8/2015 | Schultz | H04W 12/06 |
| 9,323,912 | B2 * | 4/2016 | Schultz | G06F 21/32 |
| 9,547,760 | B2 * | 1/2017 | Kang | G06F 21/32 |
| 9,781,107 | B2 | 10/2017 | White et al. | |
| 10,042,993 | B2 * | 8/2018 | Beigi | G06F 21/32 |
| 10,063,542 | B1 * | 8/2018 | Kao | G10L 17/06 |
| 10,097,914 | B2 * | 10/2018 | Petrank | G06F 3/165 |
| 10,460,095 | B2 * | 10/2019 | Boesen | H04R 1/1041 |
| 10,720,166 | B2 * | 7/2020 | Caldwell | G10L 15/30 |
| 10,915,614 | B2 * | 2/2021 | Lesso | A61B 5/12 |
| 10,984,083 | B2 * | 4/2021 | Lesso | G06F 21/32 |
| 11,042,617 | B2 * | 6/2021 | Lesso | H04R 1/1041 |
| 11,042,618 | B2 * | 6/2021 | Lesso | G10K 11/17823 |
| 11,494,473 | B2 * | 11/2022 | Mukund | H04L 9/3231 |
| 2008/0005575 | A1 * | 1/2008 | Choyi | H04M 1/67 713/182 |
| 2015/0347734 | A1 | 12/2015 | Beigi | |
| 2018/0096120 | A1 | 4/2018 | Boesen | |
| 2018/0307818 | A1 | 10/2018 | Yano et al. | |
| 2019/0012444 | A1 * | 1/2019 | Lesso | H04R 1/1041 |
| 2019/0012448 | A1 * | 1/2019 | Lesso | H04W 12/06 |

FOREIGN PATENT DOCUMENTS

| | | |
|---|---|---|
| JP | 2008-033144 A | 2/2008 |
| JP | 2015-206857 A | 11/2015 |
| JP | 2017-167884 A | 9/2017 |
| WO | 2017/069118 A1 | 4/2017 |

OTHER PUBLICATIONS

Arakawa, Takayuki, Takafumi Koshinaka, Shohei Yano, Hideki Irisawa, Ryoji Miyahara, and Hitoshi Imaoka, "Fast and Accurate Personal Authentication Using Ear Acoustics", Dec. 2016, 2016 Asia-Pacific Signal and Information Processing Association Annual Summit and Conference (APSIPA), pp. 1-4. (Year: 2016).*

Derawi, Mohammad, "Biometric Acoustic Ear Recognition", Dec. 2016, 2016 International Conference on Bio-engineering for Smart Technologies (BioSMART), pp. 1-4. (Year: 2016).*

Akkermans, Ton H.M., Tom A.M. Kevenaar, and Daniel W.E. Schobben, "Acoustic Ear Recognition for Person Identification", Nov. 2005, Fourth IEEE Workshop on Automatic Identification Advanced Technologies (AutoID'05), pp. 219-223. (Year: 2005).*

International Search Report for PCT Application No. PCT/JP2019/032729, mailed on Nov. 12, 2019.

English translation of Written opinion for PCT Application No. PCT/JP2019/032729, mailed on Nov. 12, 2019.

Ken Hanazawa, Takafumi Koshinaka, Takayuki Arakawa, "Interview Promising Public Technologies—What is Japan doing?", Defense Technology Journal, vol. 37, No. 10, Oct. 1, 2017, pp. 18-22, Japan.

Miyazaki, Taro, "High accuracy of multi-modal speaker verification using speech and pinna image information", Lecture Proceedings of 2004 Autumn Research Conference of the Acoustical Society of Japan –I–, Sep. 21, 2004, pp. 99-100, Japan.

Extended European Search Report for EP Application No. 19855693.8 dated on Aug. 31, 2021.

Arakawa, Takayuki, Takafurni Koshinaka, Shohei Yano, Hideki Irisawa, Ryoji Miyahara, and Hitoshi Imaoka, "Fast and Accurate Personal Authentication Using Ear Acoustics", Dec. 2016, 2016 Asia-Pacific Signal and Information Processing Association Annual Summit and Conference (APSIPA), pp. 1-4. (Year: 2016).

US Office Action for U.S. Appl. No. 17/270,303 mailed on Apr. 24, 2024.

US Office Action for U.S. Appl. No. 17/270,303, mailed on Mar. 15, 2024.

US Notice of Allowance for U.S. Appl. No. 18/483,896, mailed on Nov. 13, 2025.

* cited by examiner

BIOMETRIC AUTHENTICATION DEVICE, BIOMETRIC AUTHENTICATION METHOD, AND RECORDING MEDIUM

This application is a Continuation of U.S. application Ser. No. 17/270,303 filed on Feb. 22, 2021, which is a National Stage Entry of PCT/JP2019/032729 filed on Aug. 22, 2019, which claims priority from Japanese Patent Application 2018-162229 filed on Aug. 31, 2018, the contents of all of which are incorporated herein by reference, in their entirety.

TECHNICAL FIELD

The example embodiments relate to a biometric authentication device and the like for authenticating a user.

BACKGROUND ART

A personal authentication technology using biometric information on a user, such as a fingerprint, iris, face, voiceprint, and ear, has the advantage of being less likely to be leaked or stolen and not to be forgotten or lost than a password or key. For this reason, various biometric authentication approaches for authenticating users have been developed in recent years, including voiceprint (voice) authentication (hereinafter referred to as voice authentication) and otoacoustic authentication (hereinafter referred to as ear authentication).

In voice authentication, the user's voice is used for authentication. For example, in an instrument such as a smart speaker, a user performs an operation through voice interaction with an artificial intelligence (AI) agent equipped in the instrument. Voice authentication is used for purposes such as logging in to a service provided by the instrument or providing a more suitable response to an individual user from the instrument (personalizing) (see PTL 1).

In ear authentication, reverberation characteristics in an ear of a user are used for authentication. For example, a hearable device such as headphones or earphones is equipped with a microphone, and extracts the reverberation characteristics of a sound in the ear to authenticate a user. The microphone of the hearable device can also be used to simultaneously perform the above voice authentication (see PTL 2).

CITATION LIST

Patent Literature

[PTL 1] JP 2002-221990 A

[PTL 2] JP 2015-206857 A

SUMMARY OF INVENTION

Technical Problem

When the above voice authentication and ear authentication are performed independently, the authentication is not precise in some cases. For example, when the background noise is large, the accuracy of the voice authentication is lowered, and when the earphone is not sufficiently adhered to the ear, the accuracy of the ear authentication is lowered. If authentication fails, the user cannot immediately use an instrument (or function) accessible on the assumption that authentication succeeds. This could bring about fatal consequences for users who need to use the instrument immediately (for example, emergency medical personnel). Meanwhile, when voice authentication and ear authentication are simply combined, although the accuracy becomes higher, the time taken by authentication is given as the sum of times required for these approaches of authentication, and the user has to wait for a longer time.

The disclosure has been made in view of the above disadvantages, and one object of the disclosure is to provide a biometric authentication device and the like capable of performing highly accurate, quick authentication in combination of voice authentication and ear authentication.

Solution to Problem

In view of the above disadvantages, a biometric authentication device according to a first aspect of the disclosure includes:

a replay means reproducing a sound;

an ear authentication means acquiring a reverberation sound of the sound output from the replay means in an ear of a user to be authenticated, extracting an ear acoustic feature from the reverberation sound, and calculating an ear authentication score by comparing the extracted ear acoustic feature with an ear acoustic feature stored in advance;

a voice authentication means extracting a talker feature from a voice of the user that has been input, and calculating a voice authentication score by comparing the extracted talker feature with a talker feature stored in advance; and an authentication integration means outputting an authentication integration result calculated based on the ear authentication score and the voice authentication score, wherein after the sound is output into the ear by the replay means, the voice of the user is input.

A biometric authentication method according to a second aspect of the disclosure includes:

acquiring a reverberation sound of a sound output from a replay means in an ear of a user to be authenticated, extracting an ear acoustic feature from the reverberation sound, and calculating an ear authentication score by comparing the extracted ear acoustic feature with an ear acoustic feature stored in advance;

extracting a talker feature from a voice of the user that has been input, and calculating a voice authentication score by comparing the extracted talker feature with a talker feature stored in advance; and outputting an authentication integration result calculated based on the ear authentication score and the voice authentication score, wherein after the sound is output into the ear by the replay means, the voice of the user is input.

A biometric authentication program according to a third aspect of the disclosure includes:

acquiring a reverberation sound of a sound output from a replay means in an ear of a user to be authenticated, extracting an ear acoustic feature from the reverberation sound, and calculating an ear authentication score by comparing the extracted ear acoustic feature with an ear acoustic feature stored in advance;

extracting a talker feature from a voice of the user that has been input, and calculating a voice authentication score by comparing the extracted talker feature with a talker feature stored in advance; and outputting an authentication integration result calculated based on the ear authentication score and the voice authentication score, the biometric authentication program causing a computer to enable that after the sound is output into the ear by the replay means, the voice of the user is input.

The program may be stored on a non-transitory computer-readable storage medium.

Advantageous Effects of Invention

According to the disclosure, a biometric authentication device and the like capable of performing highly accurate, quick authentication in combination of voice authentication and ear authentication can be provided.

EXAMPLE EMBODIMENT

Hereinafter, several example embodiments will be described in detail with reference to the drawings.

First Example Embodiment

Biometric Authentication Device

Figure 1:
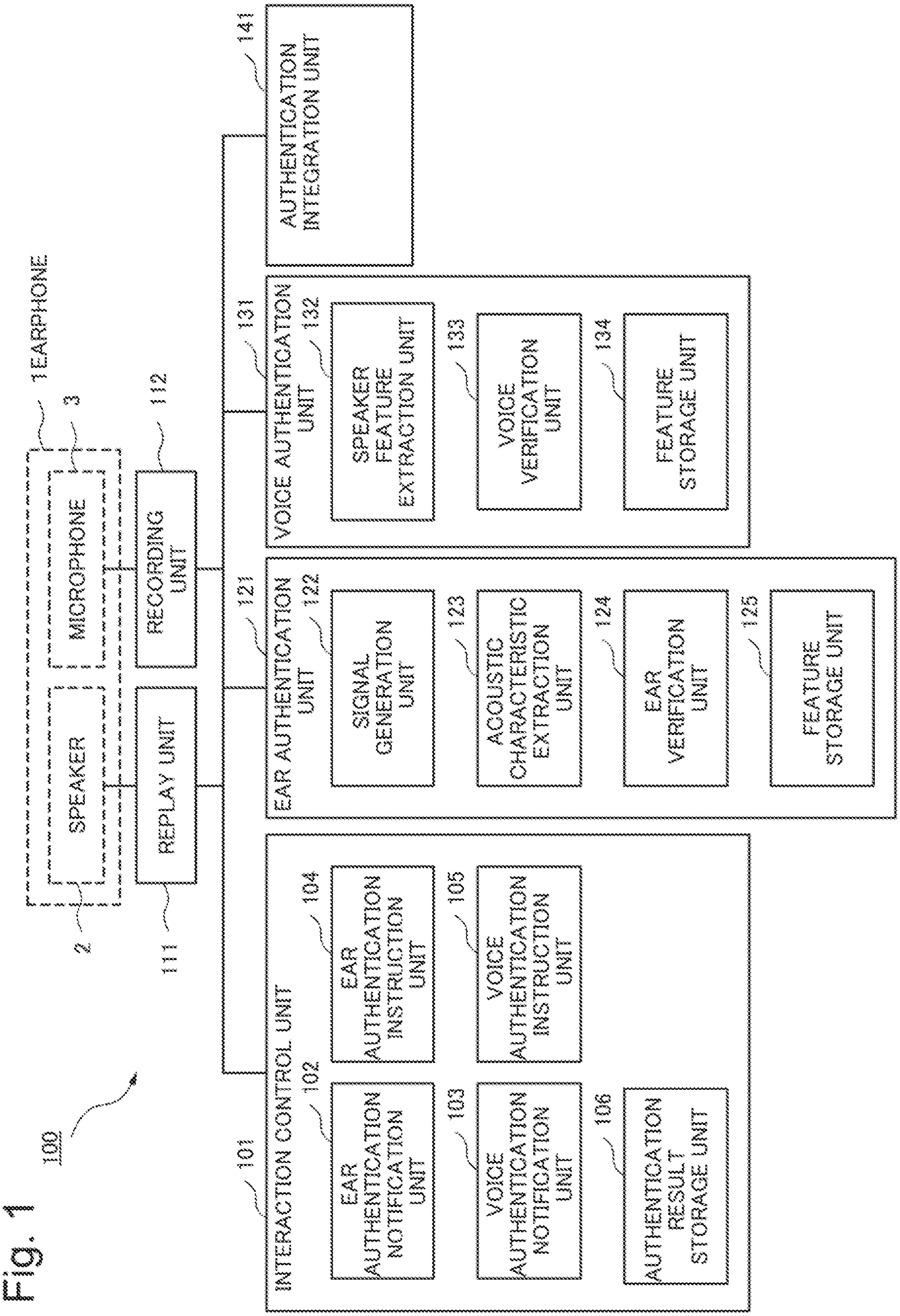
FIG. 1 is a configuration diagram of a biometric authentication device according to a first example embodiment of the disclosure.

A biometric authentication device 100 according to a first example embodiment will be described with reference to FIG. 1. The biometric authentication device 100 is equipped with an electronic circuit incorporating a voice authentication process, an ear authentication process, and a process of integrating results of both of the processes. Alternatively, a program for executing these processes may be implemented by being installed in a communication instrument (such as a smartphone) owned by a user. As illustrated in FIG. 1, the biometric authentication device 100 is connected to an earphone 1 built with a speaker 2 and a microphone 3 via a wired cable or wireless communication. The speaker 2 is connected to a replay unit 111 of the biometric authentication device 100. The microphone 3 is connected to a recording unit 112 of the biometric authentication device 100.

Figure 2:
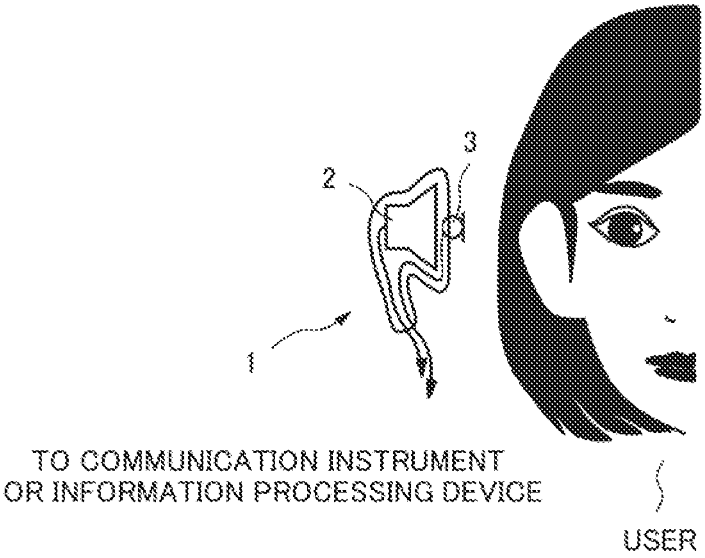
FIG. 2 is a configuration diagram of an earphone.

As illustrated in FIG. 2, the biometric authentication device 100 may be equipped on the earphone 1 built with the speaker 2 and the microphone 3.

The speaker 2 outputs a sound to a user side. In ear authentication, the microphone 3 inputs a reverberation sound from an ear side of the user while the user is wearing the earphone 1. In voice authentication, the microphone 3 inputs a speaking of the user while the user is wearing the earphone 1. When it is difficult to pick up the user's voice during voice authentication, the user may move the earphone 1 near the mouth or the like. The microphones 3 may be prepared separately for voice authentication and ear authentication. For example, using an earphone on a headset side, a microphone for ear authentication may be equipped inside the earphone 1, and a microphone alone such as an earphone microphone may be fixed near the mouth of the user as a microphone for voice authentication.

The communication instrument (not illustrated) owned by the user may be equipped with an AI interaction program. The AI interaction program can be operated in cooperation with various applications, and is capable of acquiring various types of information and executing various application functions through interaction using voice. The voice on the AI side is delivered to the user via the speaker 2 built in the earphone 1, and the voice on the user side is delivered to the AI interaction program via the microphone 3 built in the earphone 1. The above-mentioned information acquisition and function execution includes information and functions that are only permitted to be accessed by an authorized user. Examples of the above include functions that require strong security to protect personal information, such as connecting to an email account and a bank account. When requested by the user to access such a function, the AI interaction program activates the biometric authentication device 100 to manage the access.

As illustrated in FIG. 1, the biometric authentication device 100 according to the first example embodiment includes an interaction control unit 101, the replay unit 111, the recording unit 112, an ear authentication unit 121, a voice authentication unit 131, and an authentication integration unit 141.

The interaction control unit 101 controls in such a way that, after the replay unit 111 outputs a sound into the user's ear, the recording unit 112 inputs (records) the user's voice. The interaction control unit 101 includes an ear authentication notification unit 102, a voice authentication notification unit 103, an ear authentication instruction unit 104, a voice authentication instruction unit 105, and an authentication result storage unit 106.

The ear authentication notification unit 102 notifies the user that ear authentication (or both of ear authentication and voice authentication) will begin. Specifically, the ear authentication notification unit 102 causes the replay unit 111 to reproduce a voice (which can be a recorded voice) for letting the user know that the authentication is to start.

The voice authentication notification unit 103 notifies the user that voice authentication will begin. Specifically, the voice authentication notification unit 103 causes the replay unit 111 to reproduce a voice (which can be a recorded voice) for letting the user know that authentication is to start.

The ear authentication instruction unit 104 instructs the ear authentication unit 121 to start ear authentication.

The voice authentication instruction unit 105 instructs the voice authentication unit 131 to start voice authentication. The voice authentication instruction unit 105 or the voice authentication unit 131 may generate a one-time password that can be used only for a predetermined time. The generated one-time password is delivered to the user by voice via the earphone 1, or is delivered to the user by being displayed on a display or the like of the user's communication instrument (not illustrated).

The authentication result storage unit 106 stores verification scores notified from the ear authentication unit 121 and the voice authentication unit 131.

The replay unit 111 reproduces (outputs) a recorded sound. The replay unit 111 may include a storage unit for storing a sound to be reproduced.

The recording unit 112 records a sound that is input. The recording unit 112 may include a storage unit for storing a recorded sound.

The ear authentication unit 121 includes a signal generation unit 122, an acoustic characteristic extraction unit 123, an ear verification unit 124, and a feature storage unit 125.

The signal generation unit 122 generates a sound (such as a probe signal) to be output from the replay unit 111. This sound is output to acquire a reverberation sound in the ear of the user to be authenticated.

The acoustic characteristic extraction unit 123 acquires the reverberation sound in the ear of the user to be authenticated, via the recording unit 112, and extracts acoustic characteristics relevant to the ear shape of the user from the acquired reverberation sound.

The ear verification unit 124 verifies whether acoustic characteristics of the user to be authenticated, which are stored in advance in the feature storage unit 125, coincide with the extracted acoustic characteristics. The result of the verification is output as a verification score (ear authentication score).

The feature storage unit 125 stores the acoustic characteristics of the user to be authenticated, which have been acquired in advance.

The voice authentication unit 131 includes a speaker feature extraction unit 132, a voice verification unit 133, and a feature storage unit 134.

The speaker feature extraction unit 132 extracts a talker feature from the voice of the user recorded via the recording unit 112.

The voice verification unit 133 verifies whether a talker feature of the user to be authenticated, which is stored in advance in the feature storage unit 134, coincides with the extracted talker feature. The result of the verification is output as a verification score (voice authentication score).

The feature storage unit 134 stores the talker feature of the user to be authenticated, which has been acquired in advance.

The authentication integration unit 141 calculates and outputs an authentication integration result, based on the ear authentication score and the voice authentication score.

The authentication integration result to be output is passed to a program that manages access to the secured instrument or function, such as the aforementioned AI interaction program. If the authentication integration result is equal to or more than a predetermined value, the AI interaction program permits access to a function desired by the user and terminates the biometric authentication device 100.

(Operation of Biometric Authentication Device)

Figure 3:
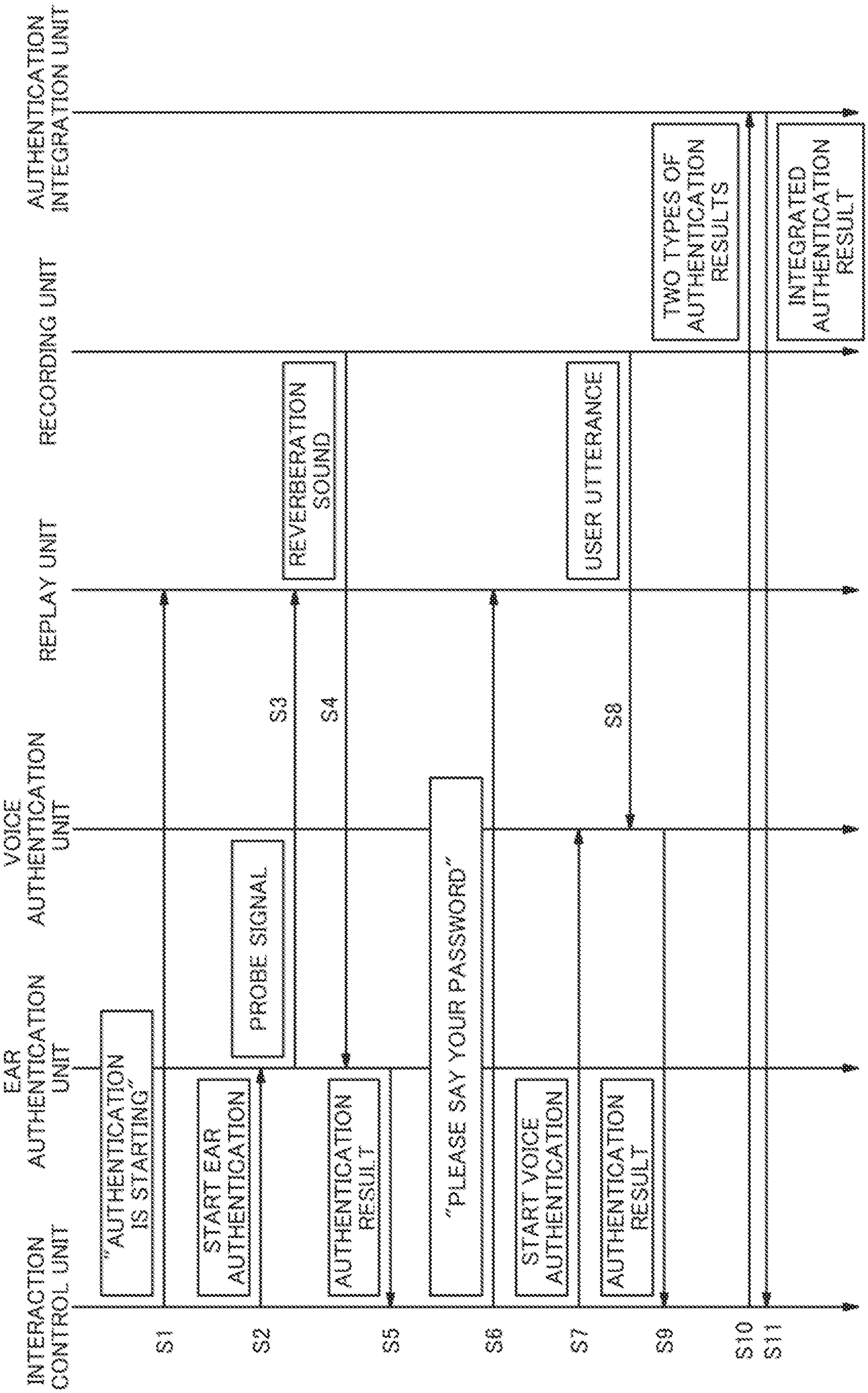
FIG. 3 is a sequence chart illustrating the operation of the biometric authentication device according to the first example embodiment of the disclosure.

The operation of an authentication process of the biometric authentication device 100 according to the first example embodiment will be described below with reference to the sequence chart illustrated in FIG. 3.

First, in step S1, when the interaction control unit 101 receives the fact that biometric authentication is required due to a request or the like from the user, the ear authentication notification unit 102 of the interaction control unit 101 instructs the replay unit 111 to reproduce a voice for notifying the user of the start of ear authentication and voice authentication. The replay unit 111 reproduces a voice (for example, "ear authentication is starting and then voice authentication will follow") for notifying the user of the start of ear authentication and voice authentication, in line with the instruction. The notification may be made not only by voice but also on a screen. For example, when the user owns a communication instrument (not illustrated) provided with a display unit, "authentication is starting" may be displayed on the provided display unit.

In step S2, the ear authentication instruction unit 104 instructs the ear authentication unit 121 to start ear authentication. Upon receiving this instruction, the signal generation unit 122 of the ear authentication unit 121 generates a probe signal and sends the generated probe signal to the replay unit 111.

In step S3, the replay unit 111 transmits the probe signal to the speaker 2, and the speaker 2 reproduces the transmitted probe signal. The probe signal may be an audible sound such as a beep sound or a melody, or may be a white noise. The probe signal may be a non-audible sound such as ultrasound.

In step S4, the recording unit 112 records a reverberation sound of the reproduced probe signal in the user's ear via the microphone 3, and sends the recorded data to the ear authentication unit 121. The ear verification unit 124 of the ear authentication unit 121 performs an ear authentication process using the recorded data. In the ear authentication process, the ear verification unit 124 estimates a transfer function in the ear using the probe signal and the reverberation sound. The ear verification unit 124 may further compress the transfer function into a low-dimensional feature by principal component analysis or the like, or may convert the transfer function into a feature such as a mel-frequency cepstral coefficient (MFCC). The output thus obtained is employed as an ear acoustic feature. The ear verification unit 124 compares the obtained ear acoustic feature with another ear acoustic feature exactly of the concerned user extracted in advance by the same procedure at the time of user registration, and calculates an ear acoustic score. A Euclidean distance or a cosine distance is conceivable as a distance scale used for score calculation.

In step S5, the ear verification unit 124 sends the verification score and the like as results of the ear authentication process to the interaction control unit 101. The interaction control unit 101 temporarily stores the received verification score of the ear authentication in the authentication result storage unit 106.

In step S6, the voice authentication notification unit 103 of the interaction control unit 101 instructs the replay unit 111 to reproduce a voice for notifying the user of the start of voice authentication and a prompt for the voice authentication. At this time, since the user has already recognized in step S1 that the authentication process is being executed, it is unnecessary to make a notification directly indicating the start of execution of voice authentication, such as "voice authentication is starting", but it is sufficient to give only a specific prompt such as "please say your password". The replay unit 111 reproduces a voice for notifying the user of the start of voice authentication in line with the instruction.

As the password, a matter that is normally known only to the user (for example, "please say your mother's maiden name") may be used. Words used in voice authentication may be notified by voice (for example, "please say today's date"). Besides, the password may be displayed on the display unit (not illustrated) of the user's communication instrument in such a way that the user is notified of the password (for example, "please say the password: ABC" is displayed). The voice authentication instruction unit 105 may generate a one-time password every time a predetermined time elapses, and cause the replay unit 111 to broadcast the generated password and deliver the generated password to the user via the earphone 1 by sound, or cause the display unit (not illustrated) of the user's communication instrument to display the generated password. With this method, the degree of safety of the password can be enhanced.

In step S7, the voice authentication instruction unit 105 of the interaction control unit 101 instructs the voice authentication unit 131 to start voice authentication. Upon receiving the instruction, the voice authentication unit 131 instructs the recording unit 112 to start recording the user's speaking (password).

In step S8, the recording unit 112 records the voice of the user who has heard the voice authentication start notification and started an utterance via the microphone 3, and sends the recorded data to the voice authentication unit 131.

In step S9, the voice authentication unit 131 performs the voice authentication process using the received recorded data. The voice authentication unit 131 extracts the talker feature such as an i-vector from the recorded voice uttered by the user. The talker feature may be extracted using a neural network capable of identifying the talker. Furthermore, the extracted talker feature is compared with another talker feature exactly of the concerned user extracted in advance by the same procedure at the time of user registration, and the verification score is calculated. A cosine distance, probabilistic linear discriminant analysis (PLDA), and the like are used for score calculation. Prior to the calculation of these scores, preprocesses such as average normalization, whitening, and norm normalization may be performed. After the voice authentication process, the voice authentication unit 131 sends the voice authentication results such as the verification score to the interaction control unit 101.

In step S10, once the interaction control unit 101 receives two types of authentication results (verification scores) for ear authentication and voice authentication, the interaction control unit 101 sends these authentication results to the authentication integration unit 141.

In step S11, the authentication integration unit 141 integrates both of the authentication results, and finally examines whether the user being authenticated is exactly the concerned user or another person. For the integration of the verification scores, any score integration approach such as a score average or a weighted average may be used. The authentication integration unit 141 determines whether the calculated authentication integration score exceeds a preset threshold value, and determines that the authentication is successful when the calculated authentication integration score exceeds the threshold value, while determining that the authentication is failed when the calculated authentication integration score does not exceed the threshold value. When notified from the user or another constituent member that there is an abnormality or defect in either the ear authentication or the voice authentication, the interaction control unit 101 may instruct the authentication integration unit 141 to weight a verification score for which the authentication has been successfully completed. The determination result is transmitted to the interaction control unit 101 as the authentication integration result. When the authentication integration result indicates the successful authentication, the interaction control unit 101 notifies the AI interaction program or the like that manages access that the user is permitted to acquire the information or execute the function as requested. When the authentication integration result indicates the authentication failure, the above AI interaction program or the like is notified to that effect. At this time, the interaction control unit 101 may notify the user of the authentication integration result via the earphone 1 or the like.

As described above, the operation of the authentication process of the biometric authentication device 100 is ended.

In the example embodiment, the description has been given assuming a process (program) that operates in the communication instrument possessed by the user, but this is not limited to the process in the portable communication instrument. For example, the program for the authentication process may be implemented in a server, and the communication instrument of the user may receive only the authentication integration result from the server via a network. Alternatively, the earphone 1 may be directly equipped with an instrument or component capable of executing the program.

Effects of First Example Embodiment

The biometric authentication device 100 according to the example embodiment can perform authentication with higher accuracy in combination of voice authentication and ear authentication. This is because the authentication integration unit 141 calculates and outputs the authentication integration result based on the ear authentication score output from the ear authentication unit 121 and the voice authentication score output from the voice authentication unit 131. When voice authentication and ear authentication are performed independently, the accuracy of authentication is lowered due to a variety of circumstances. However, the biometric authentication device 100 executes voice authentication and ear authentication using the biometric information on the user acquired via the earphone 1, and uses the authentication integration result of the voice authentication and the ear authentication, thereby being able to authenticate the user without lowering the accuracy. Moreover, the biometric authentication device 100 integrates the verification results of both of the voice authentication and the ear authentication, thereby being able to obtain a higher authentication accuracy as compared with the case of performing either authentication.

In the biometric authentication device 100, the voice authentication process is executed after the ear authentication process, that is, at least, the voice of the user is input by the recording unit 112 after a sound is output into the ear by the replay unit 111. With this procedure, the authentication process can be completed earlier as a whole than in a normal device in which the ear authentication process and the voice authentication process are simply combined, which in turn can make the waiting time of the user shorter.

Second Example Embodiment

In the first example embodiment, the user is notified by voice twice, namely, at the start of ear authentication and at the start of voice authentication. In the example embodiment, an approach for shortening the overall time required for authentication by reducing the number of times of notification to the user will be described.

(Biometric Authentication Device)

Figure 4:
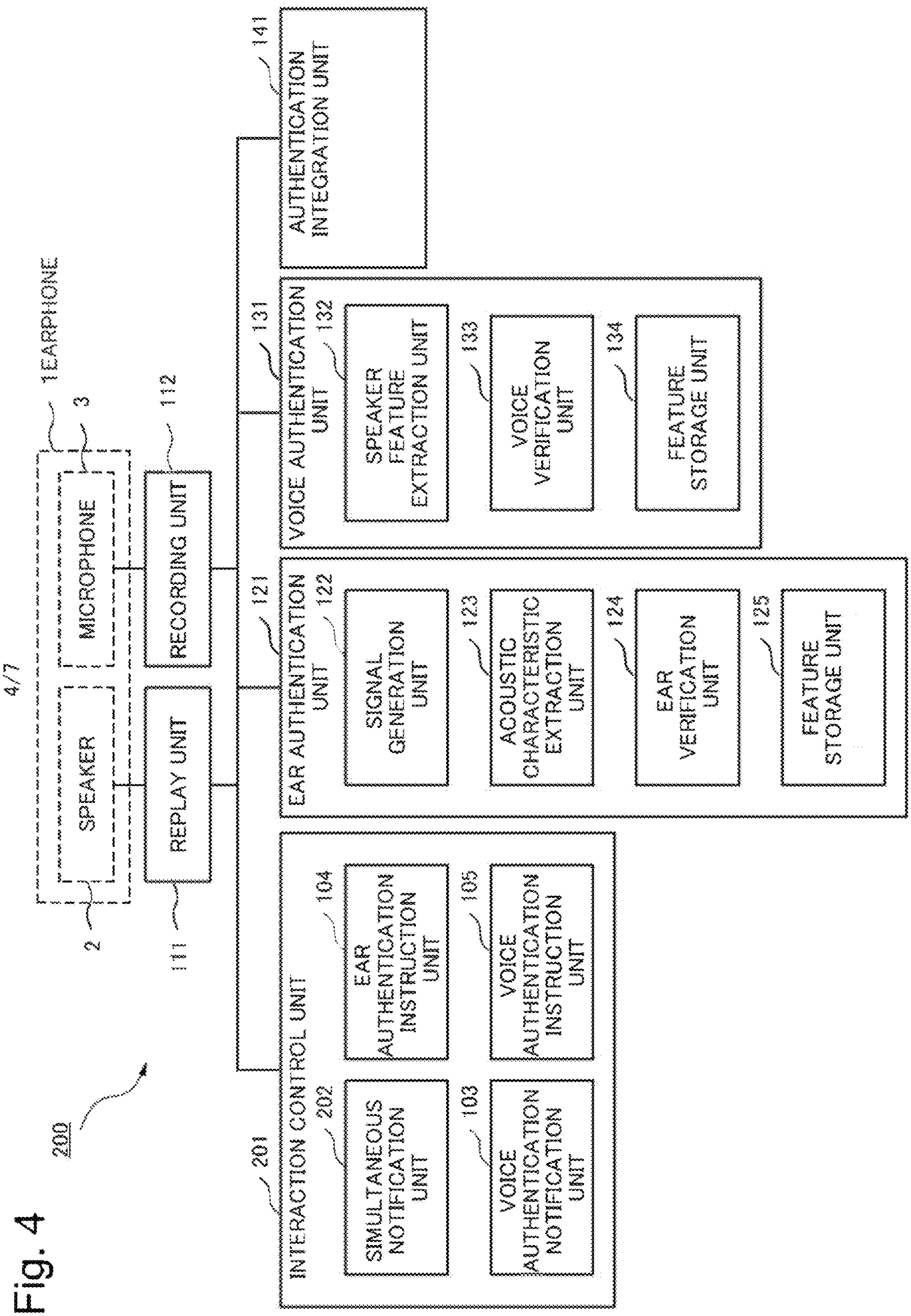
FIG. 4 is a configuration diagram of a biometric authentication device according to a second example embodiment of the disclosure.

As illustrated in FIG. 4, a biometric authentication device 200 according to the example embodiment includes an interaction control unit 201, a replay unit 111, a recording unit 112, an ear authentication unit 121, a voice authentication unit 131, and an authentication integration unit 141.

The interaction control unit 201 includes a simultaneous notification unit 202, a voice authentication notification unit 103, an ear authentication instruction unit 104, and a voice authentication instruction unit 105. The simultaneous notification unit 202 instructs the replay unit 111 to reproduce a prompt for letting a user perform ear authentication and voice authentication consecutively, by voice.

The other units and devices are the same as in the first example embodiment.

(Operation of Biometric Authentication Device)

An authentication operation of the biometric authentication device 200 of the example embodiment will be described with reference to the sequence chart illustrated in FIG. 5.

First, in step T1, when the interaction control unit 201 receives the fact that biometric authentication is required due to a request or the like from the user, the simultaneous notification unit 202 of the interaction control unit 201 instructs the replay unit 111 to reproduce, by voice, a prompt for letting the user perform ear authentication and voice authentication consecutively, such as "please say your password after the beep sound". This is to start voice authentication consecutively, swiftly after the generation of a probe sound for ear authentication. Although the probe signal may be a non-audible ultrasound or the like in the first example embodiment, an audible sound is used in the example embodiment. This is because, unless the audible sound is used, the user cannot know at what timing to begin uttering the password (to start voice authentication), and furthermore, the audible sound has higher accuracy in the acoustic characteristics of the reverberation sound. The replay unit 111 reproduces a voice for notifying the user of the start of ear authentication and voice authentication via a speaker 2 in accordance with the instruction.

In step T2, the ear authentication instruction unit 104 of the interaction control unit 201 instructs the ear authentication unit 121 to start ear authentication.

In step T3, a signal generation unit 122 of the ear authentication unit 121 generates a probe signal and sends the generated probe signal to the replay unit 111. The replay unit 111 reproduces the sent probe signal and outputs the reproduced probe signal to the speaker 2 of an earphone 1.

In step T4, the recording unit 112 records a reverberation sound of the reproduced probe signal in the user's ear via the microphone 3, and sends the recorded data to an ear verification unit 124.

In step T5, the ear verification unit 124 performs ear authentication using the recorded data, and sends an ear authentication result such as the verification score to the interaction control unit 201.

In step T6, once the ear authentication is completed, the voice authentication instruction unit 105 of the interaction control unit 201 instructs the voice authentication unit 131 to start voice authentication.

In step T7, the voice authentication unit 131 instructs the recording unit 112 to start recording the user's voice. The recording unit 112 records the utterance of the user who has started the utterance, in accordance with the instruction, and sends the recorded data to the voice authentication unit 131.

In step T8, the voice authentication unit 131 performs voice authentication using the recorded data, and sends a voice authentication result such as the verification score to the interaction control unit 201.

In step T9, upon receiving the authentication result (verification score) for voice authentication, the interaction control unit 201 sends the authentication results for ear authentication and voice authentication to the authentication integration unit 141.

In step T10, the authentication integration unit 141 integrates the authentication results for ear authentication and voice authentication, and outputs an authentication integration result of finally examining whether the user being authenticated is exactly the concerned user or another person, to the interaction control unit 201.

Effects of Second Example Embodiment

In the example embodiment, in addition to the effects of the first example embodiment, the overall time required for authentication can be shortened. This is because the simultaneous notification unit 202 of the interaction control unit 201 notifies the user in such a way that ear authentication and voice authentication can be performed consecutively, in other words, it is not necessary to make a notification of the start of voice authentication after the ear authentication is completed. Therefore, ear authentication and voice authentication can be performed consecutively with one prompt to the user, and the time taken to obtain the authentication integration result can be shortened.

Modification 1 of Second Example Embodiment

In the second example embodiment described above, the verification score computation for ear authentication (step T5) is followed by the voice recording for voice authentication (steps T6 and T7), but the verification score computation for ear authentication and the voice recording for voice authentication may be executed in parallel. In specific description, the ear verification unit 124 may send a reverberation sound recording completion notification to the interaction control unit 201 before ear authentication is performed, and the interaction control unit 201 may disclose step T6 with the reverberation sound recording completion notification as a trigger, instead of the verification score for ear authentication.

With this procedure, ear authentication and voice authentication can be performed consecutively with one prompt to the user, and the time taken to obtain the authentication integration result can be further shortened as compared with the second example embodiment.

Modification 2 of Second Example Embodiment

Figure 5:
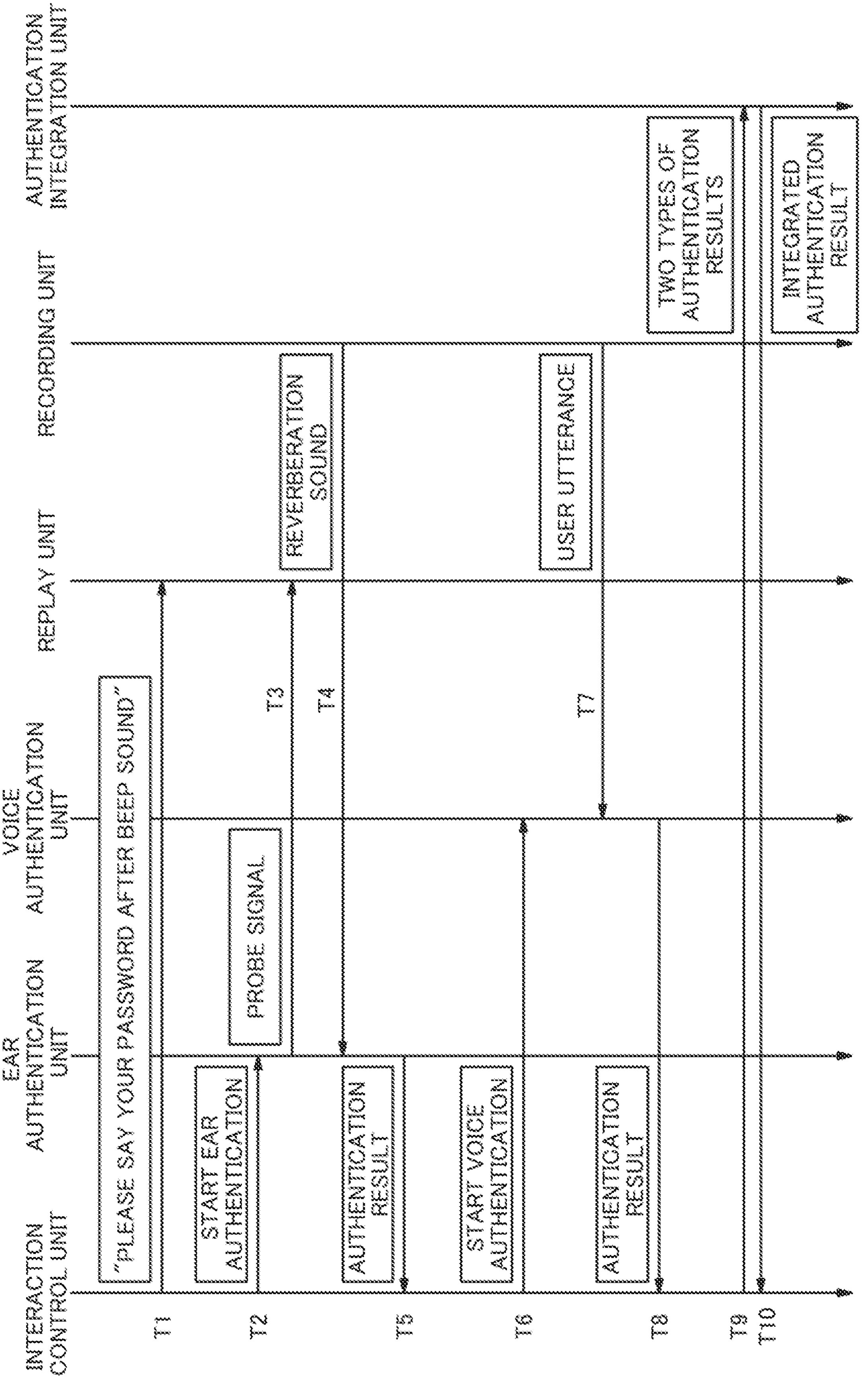
FIG. 5 is a sequence chart illustrating the operation of the biometric authentication device according to the second example embodiment of the disclosure.

By informing the user in advance that "the probe signal is a sign to start voice authentication", it is also possible to eliminate the process in step T1 illustrated in FIG. 5 (the simultaneous notification unit 202 reproduces a prompt for causing ear authentication and voice authentication to be performed consecutively, for the replay unit 111 by voice). That is, step T1 is omitted, and steps T2 to T10 are performed in the order of execution. The user may be informed by display on the display unit (not illustrated) of the communication instrument used by the user, or may be informed by hand or by a paper medium at the start of the biometric authentication device 200.

With this configuration, as compared with the second example embodiment and modification 1 of the second example embodiment, the time taken to obtain the authentication integration result can be further shortened by an amount corresponding to omitting step T1.

Modification 3 of Second Example Embodiment

Instead of step T6 (the voice authentication instruction unit 105 of the interaction control unit 201 instructs the voice authentication unit 131 to start voice authentication) illustrated in FIG. 5, the voice authentication instruction unit 105 may instructs the voice authentication unit 131 to start voice authentication after waiting for the length of continuation of the probe signal, at the same time as step T2, or immediately before or after step T2. This is because, since the probe signal has a fixed length of continuation, the waiting time is also a fixed time, and the timing of starting voice authentication can be measured. At this time, the verification score computation for ear authentication and the voice recording for voice authentication may be executed in parallel without waiting for the verification score computation result for ear authentication.

With this configuration, as compared with the second example embodiment and modification 1 of the second example embodiment, the time taken to obtain the authentication integration result can be further shortened by an amount corresponding to omitting step T6.

Third Example Embodiment

A biometric authentication device 300 according to a third example embodiment will be described with reference to FIG. 6. The biometric authentication device 300 is provided with: a replay unit 11 that reproduces a sound; a recording unit 12 that records a sound; an ear authentication unit 13 that extracts an ear acoustic feature from a reverberation sound of the sound output from the replay unit in an ear of a user to be authenticated, after the reverberation sound is recorded by the recording unit, and calculates an ear authentication score by comparing the extracted ear acoustic feature with an ear acoustic feature stored in advance; a voice authentication unit 14 that extracts a talker feature from a voice of the user that has been recorded via the recording unit, and calculates a voice authentication score by comparing the extracted talker feature with a talker feature stored in advance; and an authentication integration unit 15 that outputs an authentication integration result calculated based on the ear authentication score and the voice authentication score, in which, after the sound is output into the ear by the replay unit 11, the recording unit 12 inputs the voice of the user.

According to the third example embodiment, authentication with higher accuracy can be performed quickly in combination of voice authentication and ear authentication. This is because the authentication integration unit 15 calculates and outputs the authentication integration result, based on the ear authentication score and the voice authentication score. Furthermore, in the biometric authentication device 300, the voice authentication process is executed after the ear authentication process, that is, at least, the voice of the user is input by the recording unit 12 after a sound is output into the ear by the replay unit 11. With this procedure, the authentication process can be completed earlier as a whole than in a normal device in which the ear authentication process and the voice authentication process are simply combined.

(Information Processing Device)

Figure 6:
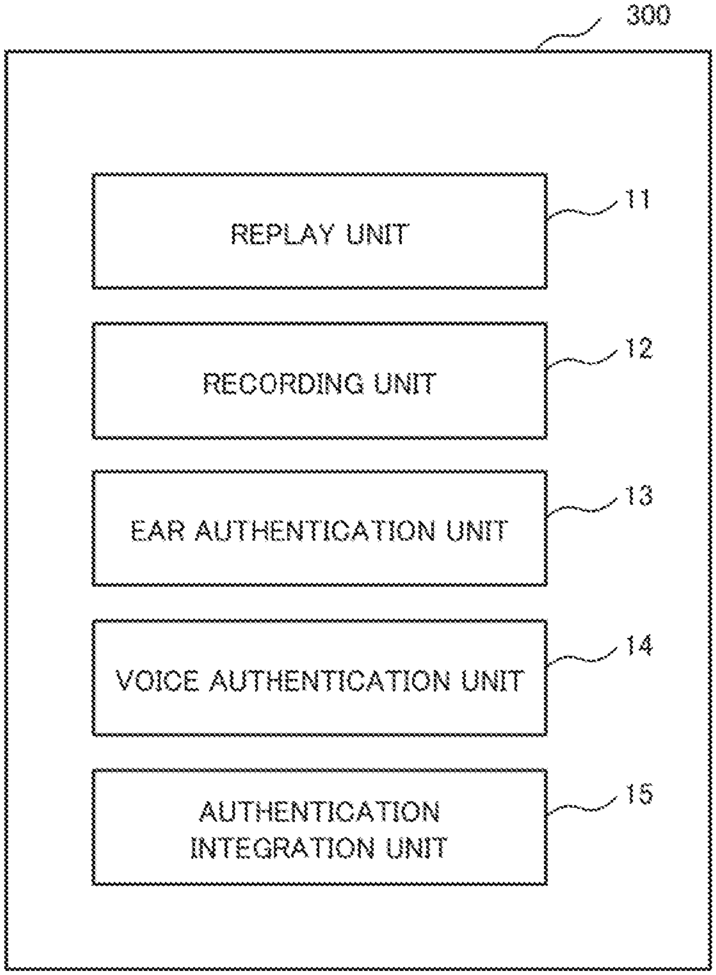
FIG. 6 is a configuration diagram of a biometric authentication device according to a third example embodiment of the disclosure.
Figure 7:
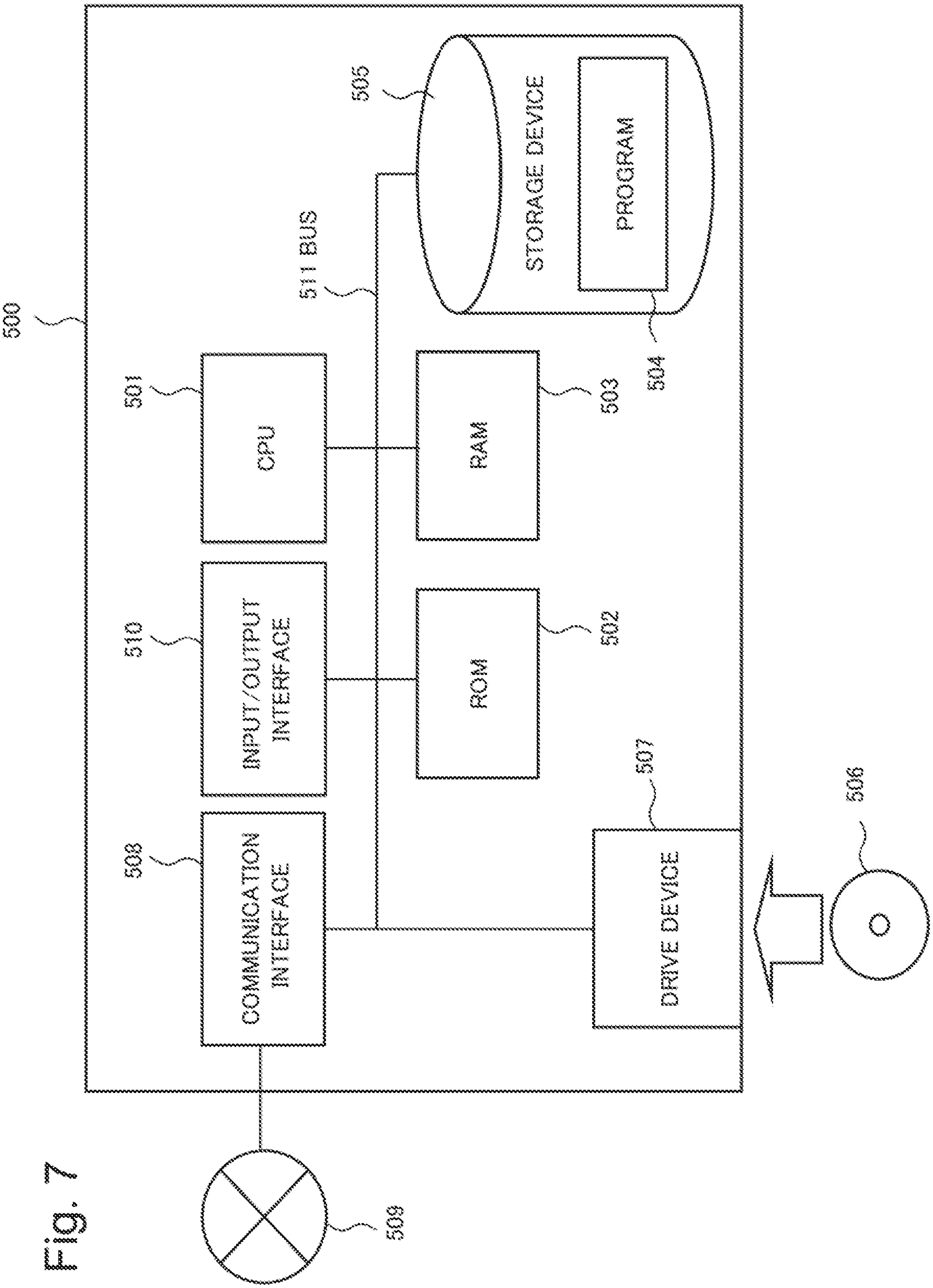
FIG. 7 is a configuration diagram of an information processing device usable in the first to third example embodiments.

In each of the above-described example embodiments, some or all of the constituent elements of the biometric authentication devices illustrated in FIGS. 1, 4, 6, and other drawings can be achieved using any combination of an information processing device 500 and a program as illustrated in FIG. 7, for example. The information processing device 500 includes, as an example, the following constituents.

- Central processing unit (CPU) 501
- Read only memory (ROM) 502
- Random access memory (RAM) 503
- Storage device 505 that stores program 504 and other data
- Drive device 507 that performs reading and writing on recording medium 506
- Communication interface 508 connected to communication network 509
- Input/output interface 510 that inputs and outputs data
- Bus 511 that connects between respective constituent elements Each constituent element of the biometric authentication device in each example embodiment of the application is achieved by the CPU 501 acquiring and executing the program 504 that enables the functions of these constituent elements. The program 504 that enables the function of each constituent element of the biometric authentication device is stored in advance, for example, in the storage device 505 or the RAM 503, and is read out by the CPU 501 as necessary. The program 504 may be supplied to the CPU 501 via the communication network 509, or may be stored in advance in the recording medium 506 in such a way as to be supplied to the CPU 501 by the drive device 507 that has read out the stored program.

The method of achieving each device has various modifications. For example, the biometric authentication device may be achieved by any combinations of information processing devices and programs that are separate from each other for each constituent element. A plurality of constituent elements included in the biometric authentication device may be achieved by any combination of one information processing device 500 and one program.

Some or all of multiple constituent elements of the biometric authentication device are achieved by other general-purpose or dedicated circuitry, a processor, or the like, or a combination thereof. These constituent elements may be constituted by a single chip or a plurality of chips connected via a bus.

Some or all of multiple constituent elements of the biometric authentication device may be achieved by a combination of the circuitry or the like described above and a program.

In a case where some or all of multiple constituent elements of the biometric authentication device are achieved by a plurality of information processing devices, pieces of circuitry, or the like, the plurality of information processing devices, pieces of circuitry, or the like may be centrally arranged or dispersedly arranged. For example, the information processing devices, pieces of circuitry, or the like may be achieved as a form in which the devices or pieces of circuitry or the like are connected with each other via a communication network, such as a client and server system or a cloud computing system.

While the invention has been particularly shown and described with reference to exemplary embodiments thereof, the invention is not limited to these embodiments. It will be understood by those of ordinary skill in the art that various changes in form and details may be made therein without departing from the spirit and scope of the example embodiments as defined by the claims.

This application is based upon and claims the benefit of priority from Japanese patent application No. 2018-162229, filed on Aug. 31, 2018, the disclosure of which is incorporated herein in its entirety by reference.

REFERENCE SIGNS LIST

1 earphone
2 speaker
3 microphone
100 biometric authentication device
101 interaction control unit
102 ear authentication notification unit
103 voice authentication notification unit
104 ear authentication instruction unit
105 voice authentication instruction unit
106 authentication result storage unit
111 replay unit
112 recording unit
121 ear authentication unit
122 signal generation unit
123 acoustic characteristic extraction unit
124 ear verification unit
125 feature storage unit
131 voice authentication unit
132 speaker feature extraction unit
133 voice verification unit
134 feature storage unit
141 authentication integration unit
200 biometric authentication device
201 interaction control unit
202 simultaneous notification unit
500 information processing device
501 CPU
503 RAM
504 program
505 storage device
506 recording medium
507 drive device
508 communication interface
509 communication network
510 input/output interface
511 bus
507 drive device
508 communication interface
509 communication network
510 input/output interface
511 bus

The invention claimed is:

1. A biometric authentication device, comprising:
a memory configured to store instructions; and
at least one processor configured to execute the instructions to perform:
reproducing a probe signal to input into an ear of a user;
extracting an ear acoustic feature of the user from a reverberation sound of the probe signal output from the ear of the user, wherein the probe signal is an audible sound that the user can hear and is to notify the user when to start speaking before recording begins;
controlling to record the reverberation sound of the probe signal and record a voice of the user successively;
extracting an ear acoustic feature from the reverberation sound, and calculating an ear authentication score by comparing the extracted ear acoustic feature with an ear acoustic feature stored in advance;
after waiting for a length of continuation of the probe signal, extracting a talker feature from the voice of the user that has been recorded, and calculating a voice authentication score by comparing the extracted talker feature with a talker feature stored in advance;
when notified from the user or another constituent member that there is an abnormality or defect in either an ear authentication or a voice authentication, weighting a result of one of the ear authentication or the voice authentication that has been successfully completed;
outputting an authentication integration result calculated based on the ear authentication score and the voice authentication score; and
starting recording the voice of the user, triggered by completion of recording the reverberation sound of the probe signal.

2. The biometric authentication device according to claim 1, wherein
the at least one processor is further configured to execute the instructions to perform:
simultaneously notifying the user of operation start of the ear authentication and the voice authentication.

3. The biometric authentication device according to claim 2, wherein
the at least one processor is further configured to execute the instructions to perform:
when either of a first authentication result based on the ear acoustic feature and a second authentication result based on the talker feature is abnormal, weighting an authentication score of either of the first authentication result and the second authentication result that is not abnormal.

4. The biometric authentication device according to claim 1, wherein
the at least one processor is further configured to execute the instructions to perform:
recording the reverberation sound and recording the voice of the user continuously; and
starting recording the voice of the user after waiting for a time length necessary for recording the reverberation sound.

5. A biometric authentication method comprising:
reproducing a probe signal to input into an ear of a user;
extracting an ear acoustic feature of the user from a reverberation sound of the probe signal output from the ear of the user, wherein the probe signal is an audible sound that the user can hear and is to notify the user when to start speaking before recording begins;
controlling to record the reverberation sound of the probe signal and record a voice of the user successively;
after waiting for a length of continuation of the probe signal, extracting an ear acoustic feature from the reverberation sound, and calculating an ear authentication score by comparing the extracted ear acoustic feature with an ear acoustic feature stored in advance;
extracting a talker feature from the voice of the user that has been recorded, and calculating a voice authentication score by comparing the extracted talker feature with a talker feature stored in advance;
when notified from the user or another constituent member that there is an abnormality or defect in either an ear authentication or a voice authentication, weighting a result of one of the ear authentication or the voice authentication that has been successfully completed;
outputting an authentication integration result calculated based on the ear authentication score and the voice authentication score;
and starting recording the voice of the user, triggered by completion of recording the reverberation sound of the probe signal.

6. The biometric authentication method according to claim 5, wherein the biometric authentication method further comprises:

simultaneously notifying the user of operation start of the ear authentication and the voice authentication.

7. The biometric authentication method according to claim 6, wherein the biometric authentication method further comprises:

when either of a first authentication result based on the ear acoustic feature and a second authentication result based on the talker feature is abnormal, weighting an authentication score of either of the first authentication result and the second authentication result that is not abnormal.

8. The biometric authentication method according to claim 5, wherein the biometric authentication method further comprises:

recording the reverberation sound and recording the voice of the user continuously; and starting recording the voice of the user after waiting for a time length necessary for recording the reverberation sound.

9. A non-transitory recording medium having a biometric authentication program stored thereon, the biometric authentication program causing a computer to perform:

reproducing a probe signal to input into an ear of a user;

extracting an ear acoustic feature of the user from a reverberation sound of the probe signal output from the ear of the user, wherein the probe signal is an audible sound that the user can hear and is to notify the user when to start speaking before recording begins;

controlling to record the reverberation sound of the probe signal and record a voice of the user successively;

extracting an ear acoustic feature from the reverberation sound, and calculating an ear authentication score by comparing the extracted ear acoustic feature with an ear acoustic feature stored in advance;

after waiting for a length of continuation of the probe signal, extracting a talker feature from the voice of the user that has been recorded, and calculating a voice authentication score by comparing the extracted talker feature with a talker feature stored in advance;

when notified from the user or another constituent member that there is an abnormality or defect in either an ear authentication or a voice authentication, weighting a result of one of the ear authentication or the voice authentication that has been successfully completed;

outputting an authentication integration result calculated based on the ear authentication score and the voice authentication score;

and starting recording the voice of the user, triggered by completion of recording the reverberation sound of the probe signal.

10. The non-transitory recording medium according to claim 9, wherein the biometric authentication program further causes the computer to perform:

simultaneously notifying the user of operation start of the ear authentication and the voice authentication.

11. The non-transitory recording medium according to claim 10, wherein the biometric authentication program further causes the computer to perform:

when either of a first authentication result based on the ear acoustic feature and a second authentication result based on the talker feature is abnormal, weighting an authentication score of either of the first authentication result and the second authentication result that is not abnormal.

12. The non-transitory recording medium according to claim 9, wherein the biometric authentication program further causes the computer to perform:

recording the reverberation sound and recording the voice of the user continuously; and starting recording the voice of the user after waiting for a time length necessary for recording the reverberation sound.

* * * * *